(12) United States Patent
Sakuta (10) Patent No.: US 7,397,888 B2
(45) Date of Patent: Jul. 8, 2008

(54) X-RAY CT APPARATUS, X-RAY DETECTOR AND METHOD OF MANUFACTURING X-RAY DETECTOR

(75) Inventor: Shigeru Sakuta, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/524,251

(22) Filed: Sep. 21, 2006

(65) Prior Publication Data

US 2007/0071163 A1    Mar. 29, 2007

(30) Foreign Application Priority Data

Sep. 22, 2005  (JP) .............................. 2005-276726

(51) Int. Cl.
*A61B 6/00*  (2006.01)
(52) U.S. Cl. .......................... 378/19; 378/98.8; 378/147
(58) Field of Classification Search ............... 378/4, 378/7, 19, 98.8, 145, 146, 147, 149, 150, 378/91, 98, 98.2; 250/363.1, 370.08, 370.09, 250/505.1
See application file for complete search history.

(56) References Cited

U.S. PATENT DOCUMENTS

| | | | | |
|---|---|---|---|---|
| 4,725,734 A | * | 2/1988 | Nishiki | 250/366 |
| 4,982,096 A | | 1/1991 | Fujii et al. | 250/367 |
| 6,188,744 B1 | | 2/2001 | Shinohara et al. | 378/8 |
| 6,393,092 B1 | * | 5/2002 | Yoshida | 378/19 |

FOREIGN PATENT DOCUMENTS

| | | |
|---|---|---|
| JP | 11-89827 | 4/1999 |
| JP | 2002-207082 | 7/2002 |

\* cited by examiner

*Primary Examiner*—Courtney Thomas
(74) *Attorney, Agent, or Firm*—Finnegan, Henderson, Farabow, Garrett & Dunner, L.L.P.

(57) ABSTRACT

An X-ray CT apparatus includes an X-ray tube configured to emit X-rays, a detector faced against the X-ray tube, the detector having a detector element with a plurality of slots and a plurality of a collimator boards inserted into the slots, a data acquisition system configured to receive data detected by the detector, a computer unit configured to reconstitute the data from the data acquisition system and a display configured to show images by the data.

12 Claims, 10 Drawing Sheets

Fig. 1

SLICE DIRECTION     CHANNEL DIRECTION

SLICE DIRECTION    CHANNEL DIRECTION

GAP CONTROL

Fig. 16

POLISHED UNDERSURFACE

X-RAY CT APPARATUS, X-RAY DETECTOR AND METHOD OF MANUFACTURING X-RAY DETECTOR

CROSS-REFERENCE TO RELATED APPLICATIONS

This application is based upon and claims the benefit of priority from Japanese Patent Application No. 2005-276726, filed on Sep. 22, 2005, the entire contents of which are incorporated herein by reference.

BACKGROUND OF THE INVENTION

1. Field of the Invention

This invention relates to an X-ray CT(computer tomography) apparatus, an X-ray detector and a method of manufacturing an X-ray detector.

2. Description of the Related Arts

In an X-ray CT apparatus, X-rays are emitted from an X-ray tube and are formed into a fan-like shaped X-ray beam by a collimator.

The X-ray tube, and a circular arc like detector and a collimator facing the X-ray tube are rotated around a target object.

The detector receives X-rays which have passed through the target object and obtains X-ray information as a signal from the received X-ray. An X-ray tomography picture of the target object is obtained by processing the X-ray information by using a computer.

Some of the X-rays emitted from the X-ray tube travel straight and penetrate the target object, and other X-rays are scattered by the target object.

Figure 17:
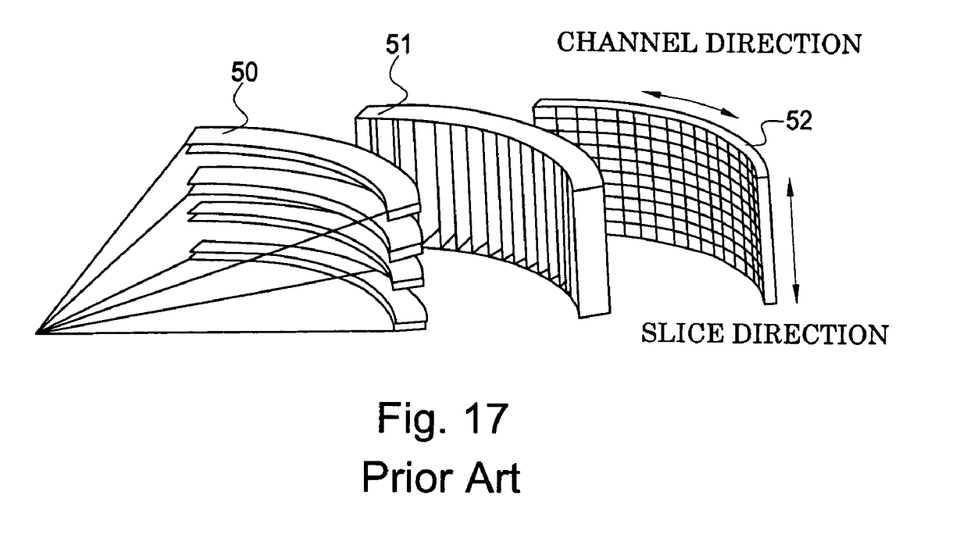
FIG. 17 is a perspective view of a conventional collimator and collimator board.
Figure 18:
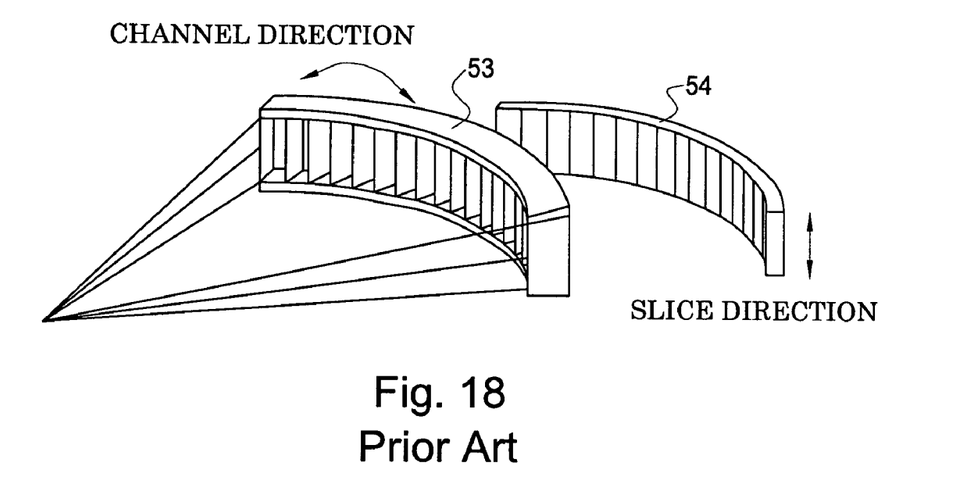
FIG. 18 is a perspective view of another conventional collimator and collimator board.

The collimator has a collimator board provided in front of the detector. The collimator removes the scattered X-rays incident from the oblique direction. The collimator passes the X-rays which have traveled straight and penetrated the target object. The collimator board forms an X-ray shield wall in front of the detector. The detector has detection elements which are arranged in a one- or two-dimensional manner. FIG. 17 and FIG. 18 show perspective views of known collimators and X-ray detectors. FIG. 17 shows a collimator having a collimator board arranged in the one-dimensional manner. FIG. 18 shows a collimator having a collimator board arranged in the two-dimensional manner.

In FIG. 17, collimator boards 50, 51 are shown together with a detection element array 52. In FIG. 18, a collimate board 53 is shown together with a detection element array 54.

The collimator arranged in one-dimension removes scattered X-rays in a certain direction, for example, a channel direction. The collimator arranged in two dimensions removes scattered X-ray in two directions, for example, channel and slice directions.

When manufacturing the X-ray detector, a collimator and an X ray detector are needed to be assembled with sufficiently accurate positioning.

This is because the collimator and the X ray detector are manufactured separately as shown in FIG. 17 or FIG. 18.

The collimator may contain a plurality of Mo(Molybdenum) boards. The X-ray detector may contain a reflector. In the assembling process, it is necessary to position the collimator and the X-ray detector with a small gap in a rotating direction.

But it takes considerable time to carry out the assembling process with high positioning accuracy.

BRIEF SUMMARY OF THE INVENTION

It is an object of the present invention to provide an X-ray CT apparatus positioning which may be manufactured with high positioning accuracy and in a relatively short time. It is another object of the present invention to provide an X-ray detector which may be manufactured with high positioning accuracy and in a relatively short time. It is further another object of the invention to provide a method of manufacturing an X-ray detector with high positioning accuracy and in a relatively short time.

1. According to one embodiment of the present invention, an X-ray CT apparatus, is provided, which includes an X-ray tube configured to emit X-rays, a detector faced against the X-ray tube, the detector having a detector element with a plurality of slots and a plurality of a collimator boards inserted into the slots, a data acquisition system configured to receive data detected by the detector, a computer unit configured to reconstitute the data from the data acquisition system and a display configured to show images by the data.

2. According to another embodiment of the present invention, an X-ray CT apparatus, is provided, which includes an X-ray tube configured to emit X-rays, a detector faced against the X-ray tube, the detector having a detection element with a plurality of first and second slots, the first slots processed in parallel with a slice direction and formed in a channel direction at a space, the second slots processed in parallel with the channel direction and formed in the slice direction at a space, a reflective and adhesive material filled in the first and second slots, a data acquisition system configured to receive data detected by the detector, a computer unit configured to reconstitute the data from a data acquisition system, a display configured to show images by the data and a plurality of collimator boards inserted into the first and second slots.

3. According to another embodiment of the present invention, an X-ray detector, is provided, which includes a detection element having a plurality of slots and a plurality of collimator boards inserted into the slots.

4. According to another embodiment of the present invention, an X-ray detector, is provided, which includes a detector element having a plurality of first slots processed in parallel with a slice direction and formed in a channel direction at a space and a plurality of second slots processed in parallel with the channel direction and formed in the slice direction at a space, a reflective and adhesive material filled in the slots and a plurality of collimator boards inserted into the first and second slots.

5. According to another embodiment of the present invention, a method of manufacturing X-ray detector, is provided, which includes processing a plurality of slots in a detection element, injecting a reflective and adhesive material into the slots, and inserting a plurality of collimator boards into the slots.

6. According to another embodiment of the present invention, a method of manufacturing X-ray detector, is provided, which includes processing a plurality of first slots parallel to a slice direction into the detection element, processing a plurality of second slots parallel to a channel direction into the detection element, injecting a reflective and adhesive material into the first slots parallel to a slice direction, injecting the reflective and adhesive material into the second slots, inserting a plurality of first collimator boards into the first slots, inserting a plurality of first collimator boards into the second slots, and polishing a field opposite to a slot formation side of the detection element.

BRIEF DESCRIPTION OF THE SEVERAL VIEWS OF THE DRAWING

The accompanying drawings, which are incorporated in and constitute a part of the specification, illustrate exemplary embodiments of the invention, and together with the general description given above and the detailed description of the embodiments given below, serve to explain the principles of the invention.

DETAILED DESCRIPTION OF THE INVENTION

Figure 1:
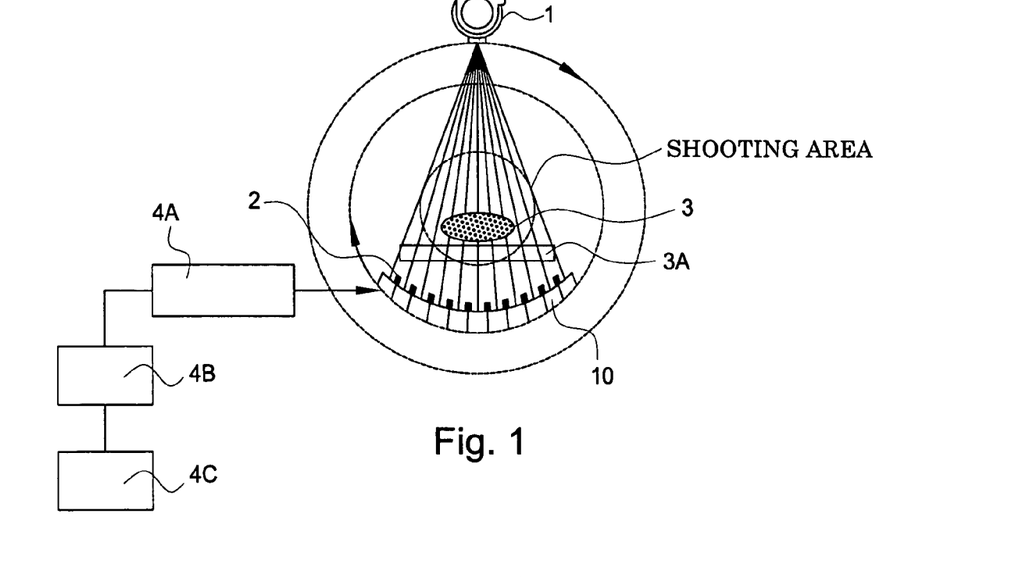
FIG. 1 is a schematic view of one embodiment of an X-ray CT apparatus in accordance with the invention.

FIG. 1 shows an X-ray CT apparatus. In FIG. 1, X-rays from an X-ray tube 1 are emitted to form a fan-like X-ray beam with a circular collimator 2.

The X-ray tube 1, a detector 10 and the circular collimator 2 facing the X-ray tube 1 are rotated around reference to a target object 3.

The detector 10 obtains X-ray information as a signal from X-rays which have passed through the target object 3. An X-ray tomography picture of the target object 3 is obtained by processing the signal by using a computer unit 4b.

Some of the X-rays emitted from the X-ray tube 1 travel straight and penetrate the target object 3, and others of the X-rays are scattered by the target object 3.

The collimator 2 has a collimator board provided in front of the detector 10. The collimator removes the scattered X-rays incident from the oblique directions. The collimator passes the X-rays which have traveled straight and penetrated the target object 3.

The collimator board functions as an X-ray shield wall in front of the detector 10 which is arranged in a one- or two-dimensional manner. The detector 10 obtains the X-ray information as a signal from received X-rays which have passed through the target object 3. The target object 3 is placed on a couch 3a.

The X-ray information is sent to a data acquisition system 4a from the detector 10. The data obtained from the data acquisition system 4a is sent to a computer unit 4b to display a tomography pictures on a display 4c. The computer unit 4b stores and reconstitutes the data. In U.S. Pat. No. 6,188,744, the entire contents of this reference being incorporated herein by reference.

Figure 2:
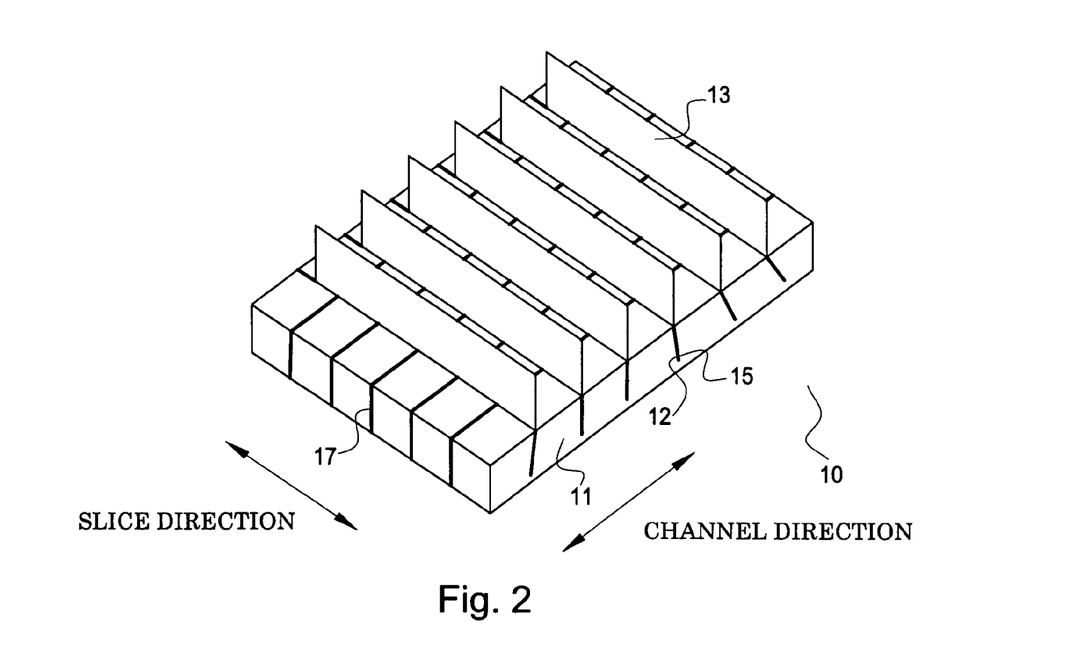
FIG. 2 is a perspective view of one embodiment of a detector in accordance with the invention.

FIG. 2 is a perspective view to show a detector 10 with a collimator arranged in the one-dimensional manner according to one embodiment of the invention.

Figure 3:
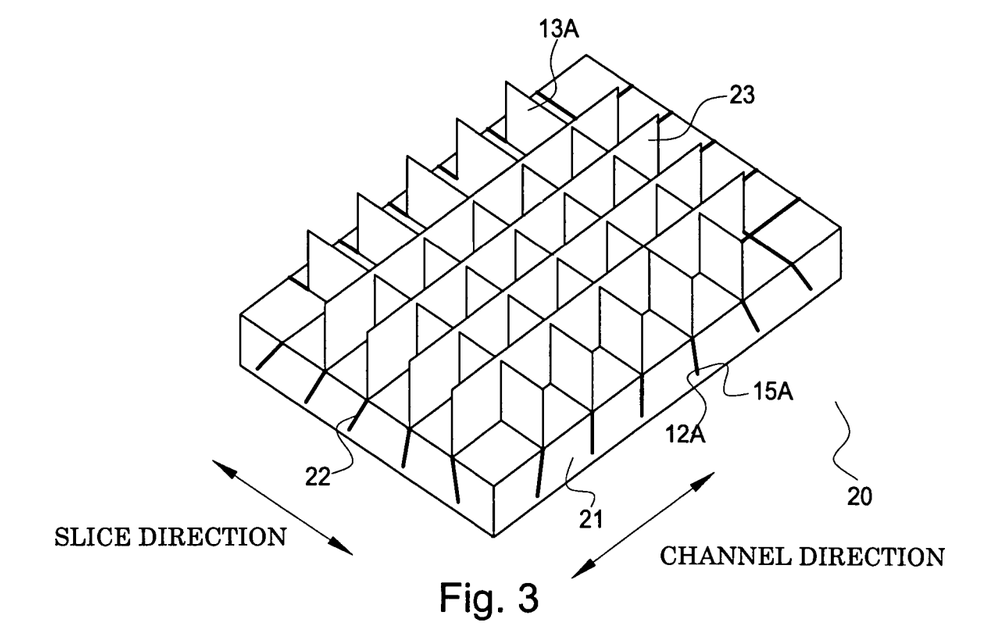
FIG. 3 is a perspective view of another embodiment of the detector in accordance with the invention.

FIG. 3 is a perspective view to show a detector 10 with a collimator arranged in the two- dimensional manner. A space between one slot and another slot may be regular or may not be regular.

In the embodiment shown in FIG. 2, laminated X-ray detection elements 11 constituting a part of the detector 10 detect the quantity of the received X-rays.

The detector 10 is made by alternately adhering slender and square shaped X-ray detection elements 11 and slender square shaped reflectors 17 (reflective material) respectively extending, in a channel direction (a rotating direction of the detector 10) and being arranged adjacently in a slice direction.

Figure 4:
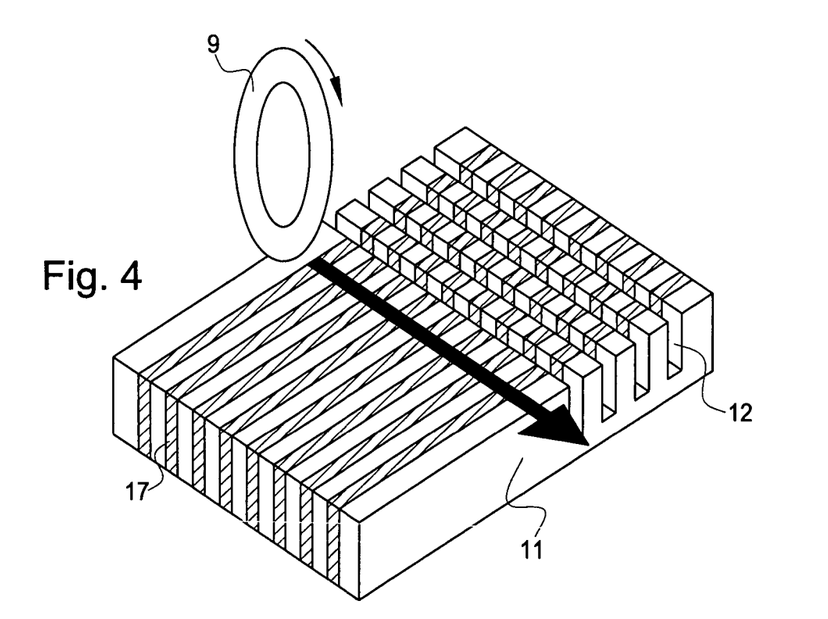
FIG. 4 is a perspective view showing slot processing for an embodiment of a detection element in accordance with the invention.

A plurality of slots 12, which have been processed in the slice direction of the laminated X-ray detection elements 11, as shown in FIG. 4, are provided in the channel direction.

The board-like X-ray shield board (collimator board) 13 is inserted in each of the slots 12. In FIG. 4, a blade 9 is used to process the slots 12.

X-rays shield boards 13 absorb the X-rays (scatted X-rays) which do not enter straight into the detector 10.

Figure 8:
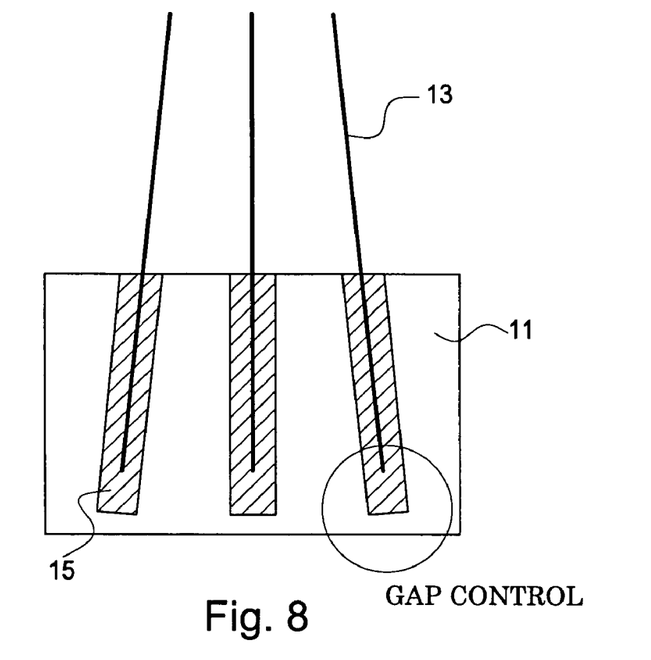
FIG. 8 is a cross-sectional view showing a collimator board inserted into a detection element of an embodiment in accordance with the invention.

The X-ray shield boards 13 are disposed so as not to contact the bottom of each of the slots 12 by gap control, as shown in FIG. 8.

The gap control is carried out so that X-ray shield boards 13 may be inserted so as not to contact the bottoms of the slots.

After inserting the X-ray shield boards 13, a back surface of the laminated elements X-ray detection elements 11 is polished with a scintillator (X-ray detection element) polishing tool as shown in FIG. 8.

Figure 6:
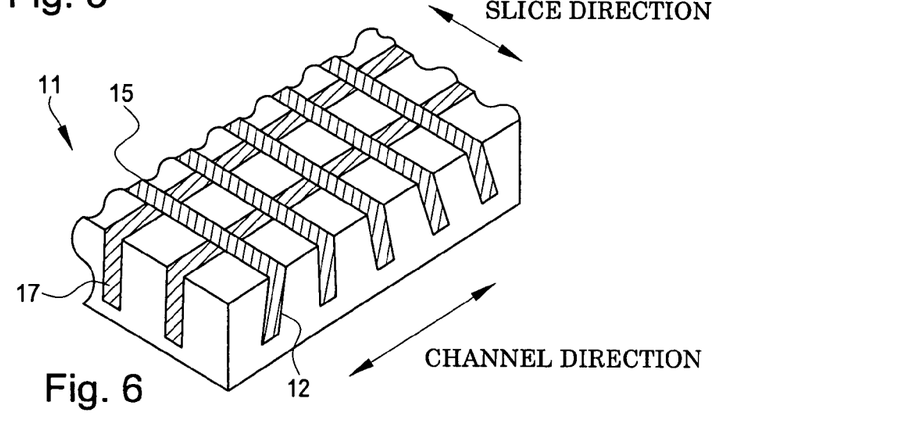
FIG. 6 is a perspective view showing an injecting reflective material serving as adhesive into a detection element of an embodiment in accordance with the invention.

If the X-ray shield boards 13 contact the bottoms of the slots 12, the back surface of the laminated X-rays detection element 11 is not polished with a scintillator polishing tool 9. This is because the X-ray shield boards 13 are made of metal which is hard and may be difficult to polish. The X-ray shield boards 13 are formed except for a polishing area. Therefore, the gap control may not always be necessary, if a polishing tool can polish the laminated elements X-ray detection elements 11 and the X-ray shield boards 13. A reflective material 15 serving as an adhesive is applied to the slots 12. The reflective material is a gel-like material. By hardening after applying the reflective material, the reflective material works like an adhesive, as shown in FIG. 6.

Before applying the reflective material 15 serving as an adhesive and hardening it, the X-ray shield boards 13 are inserted in the slots 12.

It may be unnecessary in this embodiment to carry out positioning of the reflective boards 15 and the X-ray shield boards 13 as conventional structures.

Figure 7:
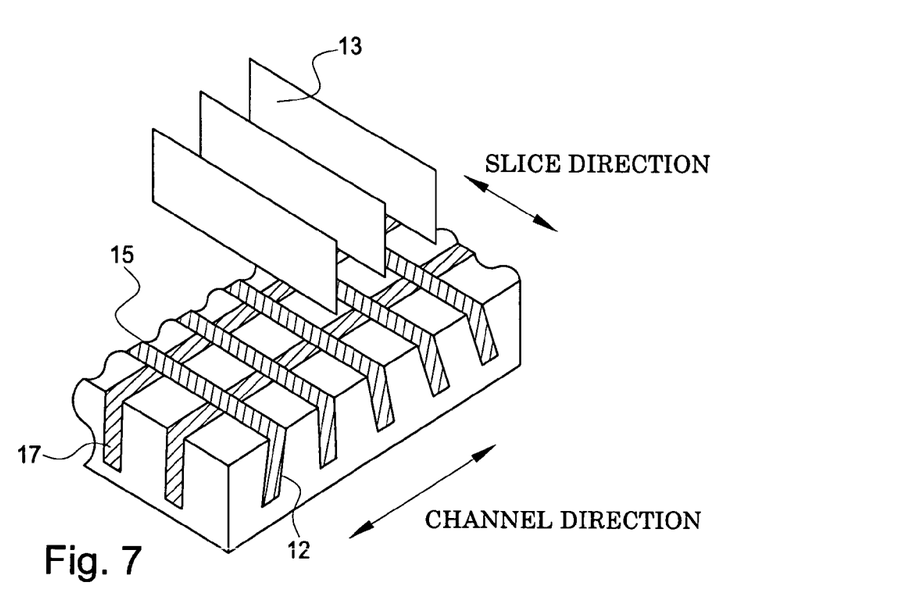
FIG. 7 is a perspective view showing inserting a collimator board into a detection element of an embodiment in accordance with the invention.

This is because the reflective material 15 serving as adhesives and the X-ray shield boards 13 are united as shown in FIG. 7.

Figure 10:
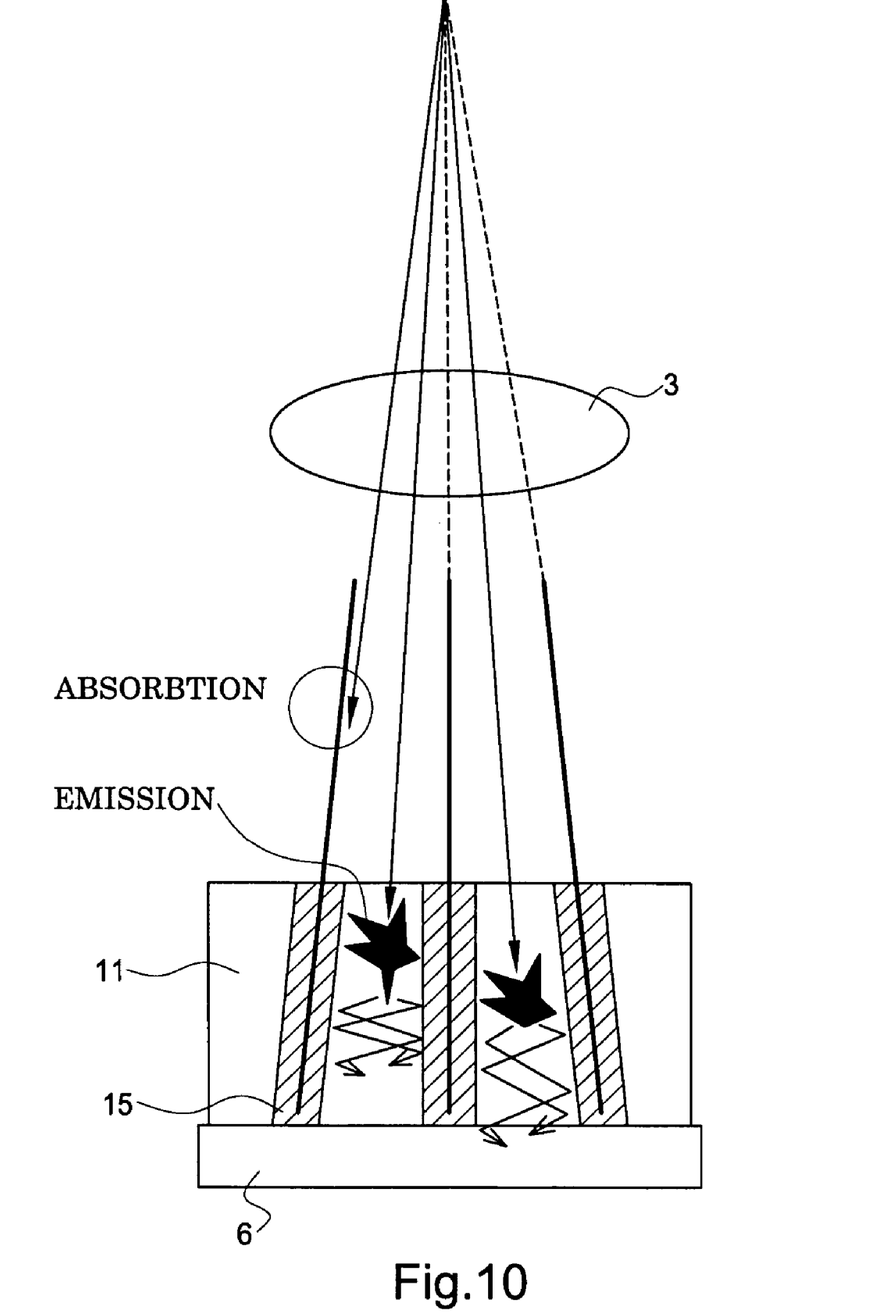
FIG. 10 is a cross-sectional view showing an X-ray passing route of an embodiment in accordance with the invention.

This structure makes it easy to have X-rays reach photodiodes 6 provided on a back side of the X-ray detection elements 11, as shown in FIG. 10. It is because X-rays reflect by the reflective material 15 in the laminated elements X-ray detection elements 11.

Scattered X-rays of the channel direction can be absorbed and removed by installing X-rays shield boards to be arranged adjacently in the slice direction perpendicular to the channel direction.

In FIG. 3, a plate-like X-ray detection element 21 is used to form X-ray shield boards 23 as well as X-ray shield boards 13a, unlike the laminated X-ray detection element in FIG. 2.

Figure 13:
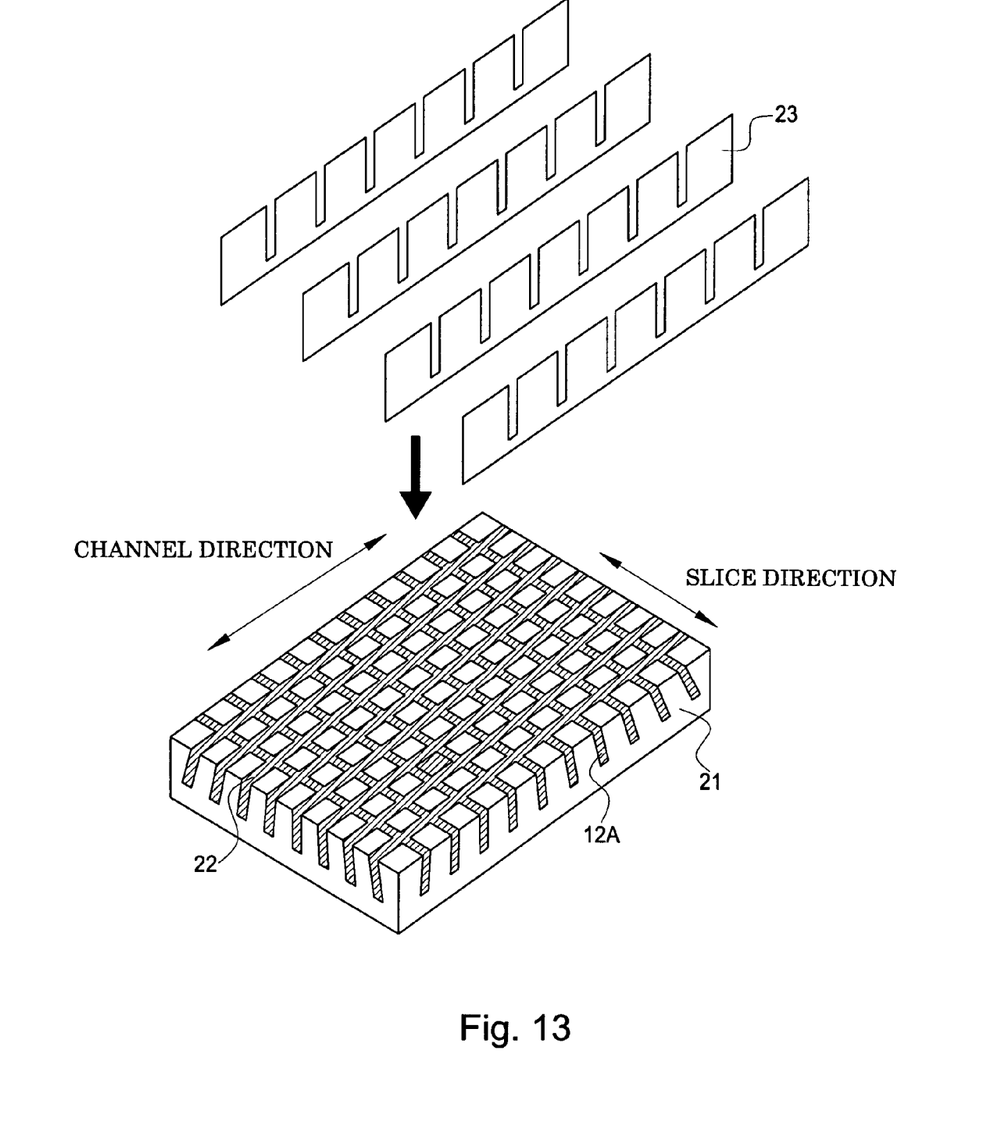
FIG. 13 is a cross-sectional view showing inserting a collimator board into a detection element of an embodiment in accordance with the invention.
Figure 14:
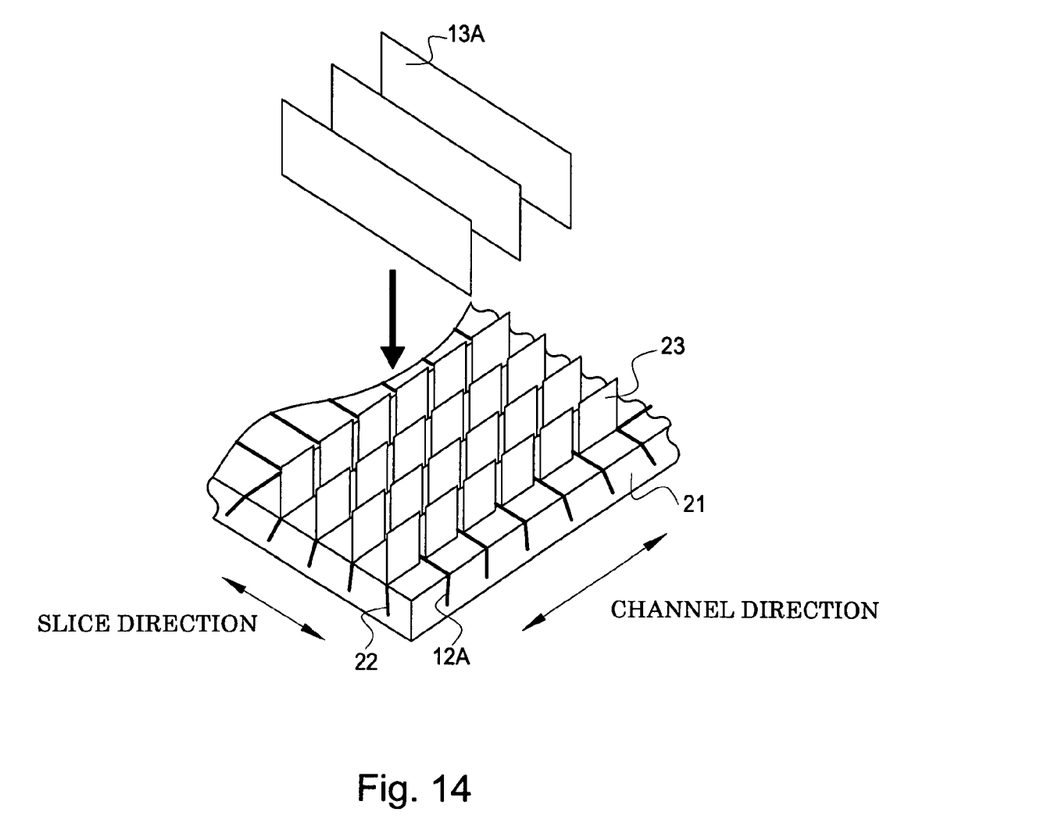
FIG. 14 is a perspective view showing a collimator board inserted into a detection element of an embodiment in accordance with the invention.

A comb-like X-ray shield boards 23 are inserted in each of a plurality of slots 22 processed into the plate-like X ray detection element 21 in the perpendicular direction of the slice direction as shown in FIG. 13. The X-rays shield boards 13 are inserted in each of the plurality of slots 12a processed into the plate-like X-ray detection element 21 in the shield direction as shown in FIG. 14.

Figure 12:
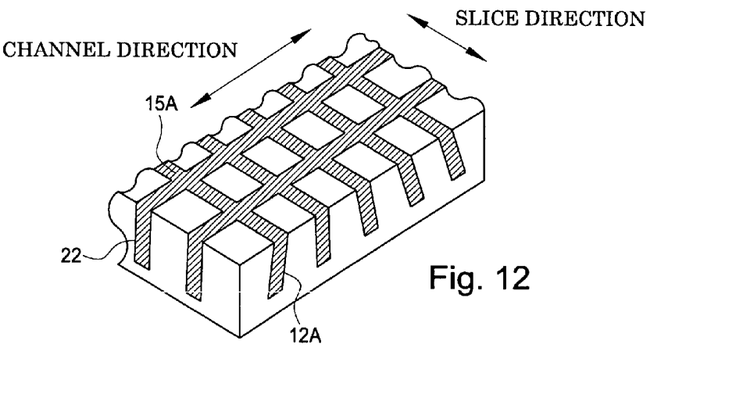
FIG. 12 is a perspective view showing an injecting reflective material serving as adhesive into a detection element of an embodiment in accordance with the invention.

Reflective material 15a serving as an adhesive is applied to the slots 22 as well as the slots 12a as shown in FIG. 12. After applying the reflective material 15a, the comb-like X-ray shield board 23 is inserted.

Figure 15:
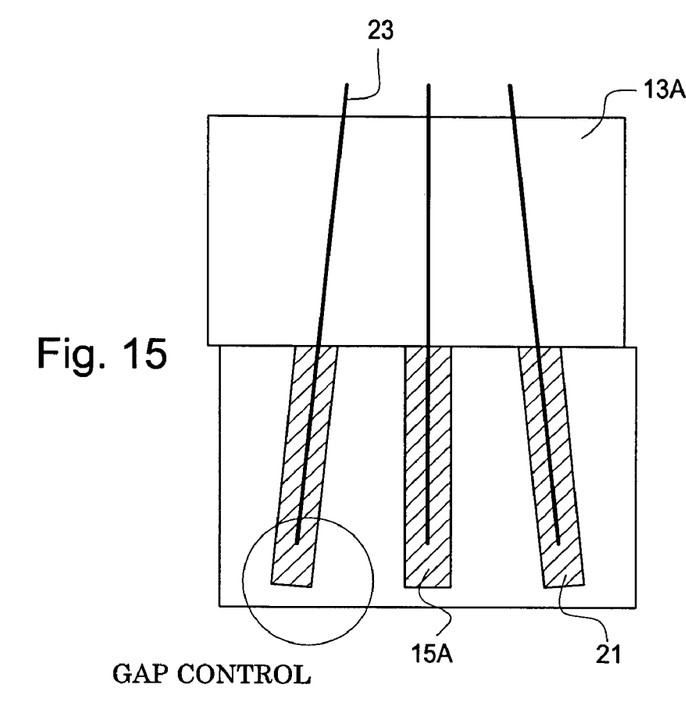
FIG. 15 is a cross-sectional view showing polishing position of a detection element of an embodiment in accordance with the invention.

It is not always necessary to carry out positioning of reflective boards and the X-ray shield boards 13a, 23 as shown in FIG. 15, unlike conventional structures.

The scattered X-rays in the channel direction may be removed by installing the X-ray shield boards 13a in the direction perpendicular in the channel direction.

Further, the scattered X-rays in the slice direction may be removed by the comb-like X-ray shield boards 23 installed in the perpendicular direction of the slice direction as shown in FIG. 10.

Though, in FIG. 3, the comb-like X-ray shield boards 23 are installed in the perpendicular direction of the slice direction, the X-ray shield boards are not restricted to the comblike structure or shape. Separate sheet-like X-ray shield boards may be used instead of the comb-like X-ray shield boards 23. Mixture of the separate sheet-like and comb-like X-ray shield boards may be used.

The board-like X-ray shield boards 13a and the comb-like X-ray shield boards 23 are made of molybdenum (Mo.), because Mo is a high rate material of X-ray interception. However, another material may be used instead of Mo.

Figure 5:
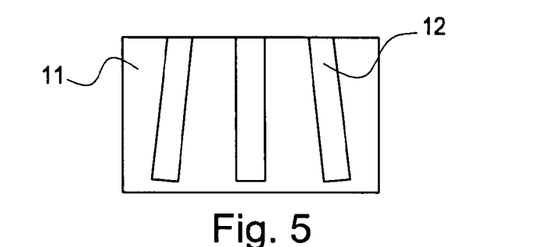
FIG. 5 is a sectional view showing slot processing of an embodiment of a detection element in accordance with the invention.

With reference to FIG. 4 to FIG. 9, a manufacturing method of the detector 10 of FIG. 2 will be explained.
(1) In FIG. 4, polishing is performed to the upper surface of a laminated elements X-ray detection elements 11, to which a reflector (reflective material) 17 is installed in the direction of a channel. The polishing is performed using whetstone or by a polishing machine to form slots 12.
(2) In FIG. 4, the slot 12 processing is provided to the direction parallel to the slice direction by using the blade 9 as the processing tool. The slots 12 are formed respectively in the direction toward an X-ray focus. The slots 12 do not reach the laminated elements X-ray detection elements 11. For example, it is left about a 0.3 mm depth remains from the undersurface of the laminated elements X-ray detection elements 11 to the slots 12 as shown in FIG. 4 and FIG. 5.

However, if the undersurface of the laminated elements X-ray detection elements 11 is fixed with wax, etc. to avoid parting, the slots 12 may reach the undersurface of the laminated elements X-rays detection elements 11.
(3) The reflective material 15 serving as an adhesive is injected into the slots 12 as shown in FIG. 6.
(4) X-ray shield boards 13 are inserted in the slots 12.

Figure 9:
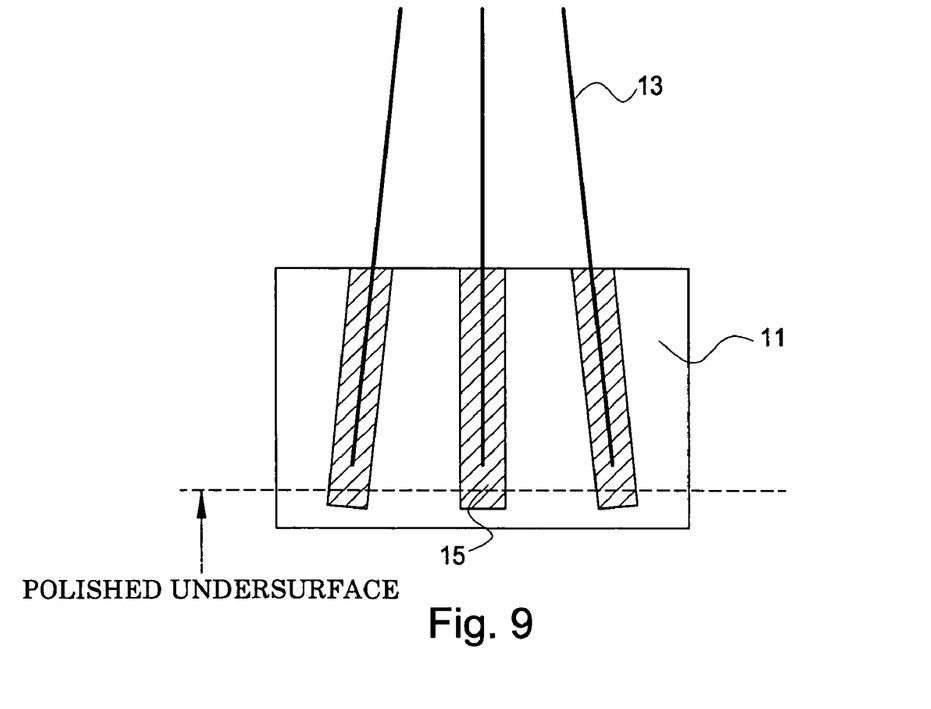
FIG. 9 is a cross-sectional view showing a polishing position of a detection element of an embodiment in accordance with the invention.

The X-ray shield boards 13 are inserted so as not to touch bottoms of the slots 12 as shown in FIG. 7 and FIG. 8.
(5) After the reflective material 15 is hardened, the undersurface of the laminated X-ray detection elements 11 are polished to the position where the reflective material 15 can be seen, as shown in FIG. 9.

Figure 11:
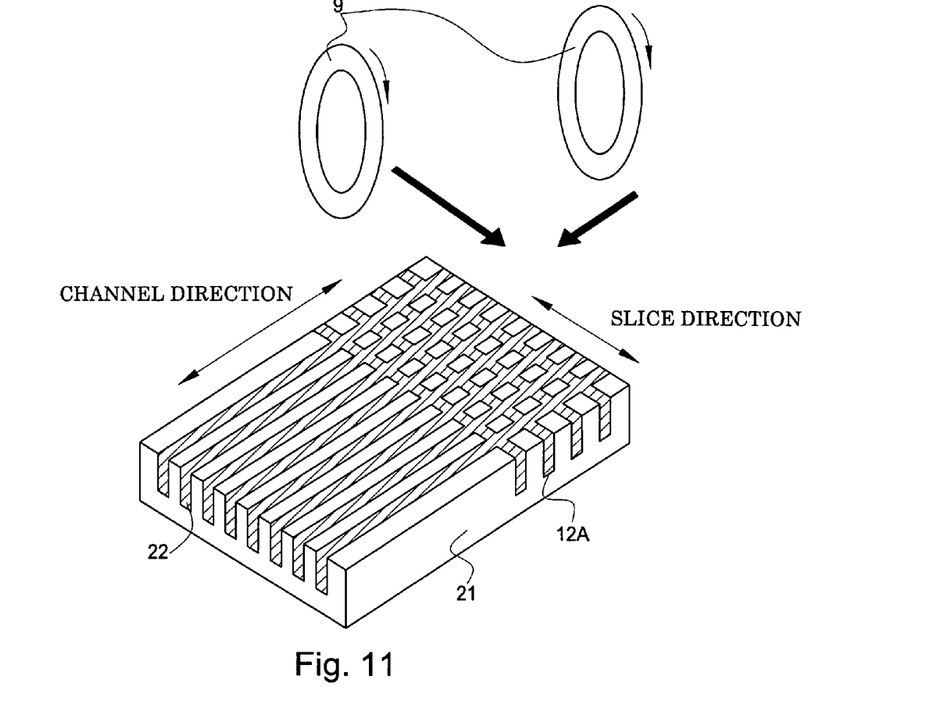
FIG. 11 is a perspective view showing slot processing for a detection element of an embodiment in accordance with the invention.

Referring to FIG. 11 to FIG. 16, the manufacturing method of the detector of FIG. 3 will be explained.
(1) As shown in FIG. 11, an upper surface of an X-ray detection element 21 is polished.
(2) The X-ray detection element 21 is polished in the channel direction and in the slice direction with the blade 9.

Slots 12a and Slots 22 are formed respectively, in the direction toward an X-ray tube focus.

The slots 12a and the slots 22 do not reach the laminated X-rays detection elements 11. For example, about a 0.3 mm depth is left from the undersurface of the laminated X-rays detection elements 11 to the slots 12a as shown in FIG. 11. The slots 12a is defined as first slots, and the slots 22 is defined as first slots.
(3) A reflective material 15 is injected into the slots 12a and the slots 22 as shown in FIG. 12.
(4) The comb-like X-ray shield boards 23 are inserted in the slots 22 after the injection. Then, the X-ray shield boards 13 are inserted into the slots 12a.

Figure 16:
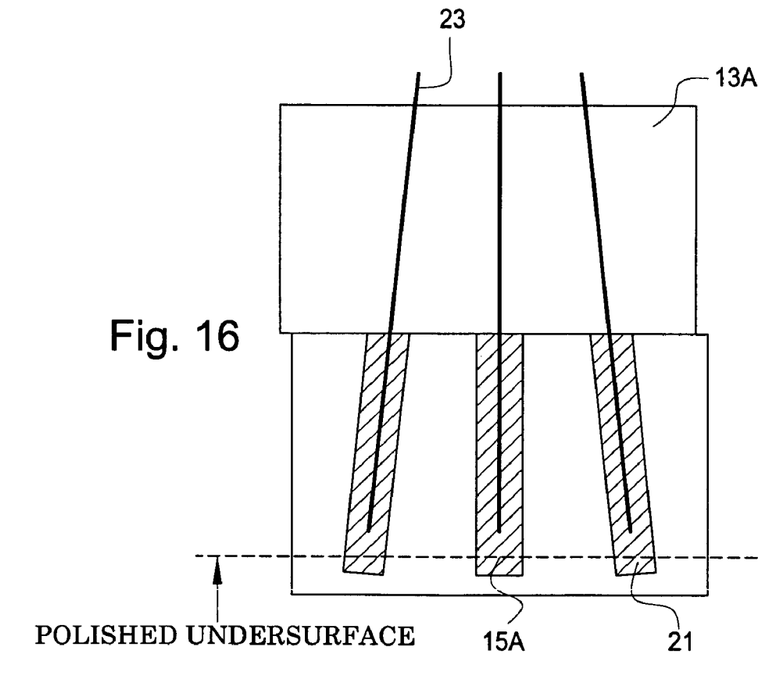
FIG. 16 is a cross-sectional view showing polishing a detection element of an embodiment of in accordance with the invention.

The X-ray shield boards 13 are provided so as not to touch bottoms of the slots 12a and the slots 22 as shown in FIG. 13, to FIG. 15.
(5) After the reflective material is hardened, the undersurfaces of the laminated X-rays detection element 21 are polished to the position where the reflective material 15 can be seen, as shown in FIG. 16).

The detector 20 in FIG. 3 can absorb and intercept not only scattered X-rays of the channel direction but also those of the slice direction, because of honeycomb structure of the detector 20, in comparison with the detector 10 in FIG. 2.

As a result, the detector 20 has a structure which can be bore during a high-speed scanning.

Because the X-ray shield boards 13a and the comb-like X-ray shield boards 23 are inserted in the X-ray detection elements 21 directly, a positioning process may be omitted to attain reducing a step of manufacturing, to increase accuracy and to improve strength.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. An X-ray CT apparatus, comprising:
an X-ray tube configured to emit X-rays;
a detector facing the X-ray tube, the detector having a detector element with a plurality of slots and a plurality of a collimator boards inserted into the slots;
a data acquisition system configured to receive data detected by the detector;
a computer unit configured to reconstitute the data from the data acquisition system; and
a display configured to show images corresponding to the data,
wherein each of the plurality of collimator boards are positioned in the plurality of slots so that none of the plurality of collimator boards contact portions of the detector element at base ends of the plurality of slots.

2. The X-ray CT apparatus according to claim 1, wherein a reflective and adhesive material is filled in the plurality of slots.

3. The X-ray CT apparatus according to claim 1, wherein the plurality of slots are parallel to a slice direction.

4. An X-ray CT apparatus, comprising:
an X-ray tube configured to emit X-rays;
a detector facing the X-ray tube, the detector having a detection element with a plurality of first and second slots, the first slots parallel to a slice direction and formed in a channel direction at a plurality of first spaces, the second slots parallel to the channel direction and formed in the slice direction at a plurality of second spaces;
a reflective and adhesive material filled in the first and second slots;
a data acquisition system configured to receive data detected by the detector;
a computer unit configured to reconstitute the data from the data acquisition system;
a display configured to show images corresponding to the data; and
a plurality of collimator boards inserted into the first and second slots,
wherein each of the plurality of collimator boards are positioned in the plurality of first and second slots so that none of the plurality of collimator boards contact portions of the detection element at base ends of the plurality of first and second slots.

5. An X-ray detector, comprising:
a detection element having a plurality of slots; and
a plurality of collimator boards inserted into the slots,
wherein each of the plurality of collimator boards are positioned in the plurality of slots so that none of the plurality of collimator boards contact portions of the detection element at base ends of the plurality of slots.

6. The X-ray detector according to claim 5, wherein a material that is reflective and adhesive is in the plurality of slots.

7. An X-ray detector according to claim 6, wherein the plurality of slots are parallel to a slice direction.

8. An X-ray detector, comprising:
a detector element having a plurality of first slots parallel to a slice direction and formed in a channel direction at a plurality of first spaces and a plurality of second slots parallel to the channel direction and formed in the slice direction at a plurality of second spaces;
a reflective and adhesive material filled in the slots; and
a plurality of collimator boards inserted into the plurality of first and second slots,
wherein each of the plurality of collimator boards are positioned in the plurality of first and second slots so that none of the plurality of collimator boards contact portions of the detector element at base ends of the plurality of first and second slots.

9. A method of manufacturing an X-ray detector comprising:
processing a plurality of slots in a detection element;
injecting a reflective and adhesive material into the slots; and
inserting a plurality of collimator boards into the slots so that none of the plurality of collimator boards contact portions of the detection element at base ends of the plurality of slots.

10. The method of manufacturing an X-ray detector according to claim 9, further comprising polishing a field that is opposite to a slot formation side of the detection element.

11. A method of manufacturing an X-ray detector according to claim 9, wherein the plurality of slots are processed in a direction parallel to a slice direction.

12. A method of manufacturing an X-ray detector comprising:
processing a plurality of first slots parallel to a slice direction of a detector element;
processing a plurality of second slots parallel to a channel direction of the detector element;
injecting a reflective and adhesive material into the first slots parallel to the slice direction;
injecting the reflective and adhesive material into the second slots;
inserting a plurality of first collimator boards into the plurality of first slots so that none of the plurality of first collimator boards contact a portion of the detector element at base ends of the plurality of slots;
inserting a plurality of second collimator boards into the plurality of second slots so that none of the plurality of collimator boards contact a portion of the detector element at base ends of the plurality of slots; and
polishing a field opposite to a slot formation side of the detector element.

* * * * *